US009155700B2

(12) United States Patent
Ronchi et al.

(10) Patent No.: US 9,155,700 B2
(45) Date of Patent: Oct. 13, 2015

(54) PROCESS FOR THE PREPARATION OF PHARMACEUTICAL SUSPENSIONS FOR INHALATION

(75) Inventors: Celestino Ronchi, Milan (IT); Giancarlo Ceschel, Milan (IT)

(73) Assignee: CHIESI FARMACEUTICI S.p.A., Parma (IT)

( * ) Notice: Subject to any disclaimer, the term of this patent is extended or adjusted under 35 U.S.C. 154(b) by 0 days.

(21) Appl. No.: 13/332,756

(22) Filed: Dec. 21, 2011

(65) Prior Publication Data
US 2012/0087957 A1 Apr. 12, 2012

Related U.S. Application Data

(62) Division of application No. 10/971,231, filed on Oct. 22, 2004, now abandoned.

(30) Foreign Application Priority Data

Oct. 22, 2003 (IT) .............................. MI03A002054

(51) Int. Cl.
| A61K 9/10 | (2006.01) |
| A61K 9/00 | (2006.01) |
| A61K 31/56 | (2006.01) |
| A61L 2/00 | (2006.01) |

(52) U.S. Cl.
CPC .................. *A61K 9/10* (2013.01); *A61K 9/0078* (2013.01); *A61L 2/0017* (2013.01)

(58) Field of Classification Search
CPC ....... A61K 9/10; A61K 9/0078; A61L 2/0017
USPC ......................................................... 424/489
See application file for complete search history.

(56) References Cited

U.S. PATENT DOCUMENTS

| 4,056,635 | A | * | 11/1977 | Glen et al. ..................... 514/731 |
| 4,391,803 | A | | 7/1983 | Fussi |
| 5,002,940 | A | | 3/1991 | Geller et al. |
| 5,091,187 | A | | 2/1992 | Haynes |
| 5,246,707 | A | | 9/1993 | Haynes |
| 5,803,966 | A | | 9/1998 | Kulshreshtha et al. |
| 5,833,891 | A | | 11/1998 | Subramaniam et al. |
| 5,874,029 | A | | 2/1999 | Subramaniam et al. |
| 6,149,864 | A | | 11/2000 | Dillow et al. |
| 6,241,969 | B1 | * | 6/2001 | Saidi et al. ..................... 424/45 |
| 6,464,958 | B1 | | 10/2002 | Bernini et al. |
| 6,607,784 | B2 | | 8/2003 | Kipp et al. |
| 2003/0003155 | A1 | | 1/2003 | Kipp et al. |
| 2003/0031719 | A1 | | 2/2003 | Kipp et al. |
| 2003/0044433 | A1 | | 3/2003 | Werling et al. |
| 2003/0059472 | A1 | | 3/2003 | Brynjelsen et al. |
| 2004/0223918 | A1 | * | 11/2004 | Pham et al. ..................... 424/45 |

FOREIGN PATENT DOCUMENTS

| DE | 33 41 001 | 5/1985 |
| EP | 0 346 953 | 10/1985 |
| JP | 34000794 | 2/1959 |
| WO | WO 90/06775 | 6/1990 |
| WO | WO 99/18971 | 4/1999 |
| WO | WO 99/32156 | 7/1999 |
| WO | WO 99/61001 | 12/1999 |
| WO | WO 00/38811 | 7/2000 |
| WO | WO 00/74651 | 12/2000 |
| WO | WO 01/07014 | 2/2001 |
| WO | WO 0110409 A1 * | 2/2001 |
| WO | WO 02/00199 | 1/2002 |
| WO | WO 02/40029 | 5/2002 |
| WO | WO 03/070285 | 8/2003 |
| WO | WO 2004/054545 | 7/2004 |
| WO | WO 2004054545 A1 * | 7/2004 |
| WO | WO 2005/004847 | 1/2005 |

OTHER PUBLICATIONS

"instantly" Merriam-Webster Online Dictionary, 2009, [online]. [retrieved on May 8, 2009]. Retrieved from the Internet: <URL: http://www.merriam-webster.com/dictionary/instantly>.
"directly" Merriam-Webster Online Dictionary, 2009, [online], [retrieved on May 8, 2009]. Retrieved from the Internet: <URL: http://www.merriam-webster.com/dictionary/directly>.
Journal of Drug Research (1969), 2(1-2), 103-8.

* cited by examiner

*Primary Examiner* — Mina Haghighatian
*Assistant Examiner* — Andriae M Holt
(74) *Attorney, Agent, or Firm* — Collard & Roe, P.C.

(57) ABSTRACT

Process for preparing sterile suspensions for inhalation comprising an active ingredient insoluble in water and wherein at least 80% of the particles of said active ingredient have a diameter between 3 and 5 μm, comprising the following stages: dissolving the active ingredient in the minimum quantity of an alcoholic solvent, optionally in the presence of a polyol and adding at least one surfactant, filtering the solution obtained in the previous stage through a sterilizing filter, adding the solution from stage (b) to sterile water under sonication to directly obtain a suspension wherein the particles have a reduced diameter.

**

PROCESS FOR THE PREPARATION OF PHARMACEUTICAL SUSPENSIONS FOR INHALATION

CROSS REFERENCE TO RELATED APPLICATIONS

This is a divisional of U.S. patent application Ser. No. 10/971,231, filed on Oct. 22, 2004, which claims priority under 35 USC 119 of Italian Patent Application No. MI2003A002054, filed on Oct. 22, 2003.

FIELD OF THE INVENTION

The invention relates to the preparation of suspended formulations useful for the administration by inhalation of drugs with, for example, anti-inflammatory, anti-asthma action, or the like.

STATE OF THE ART

Suspensions for inhalation based on corticosteroids to treat asthma are generally formulated by suspending liposoluble active substances in aqueous solutions, often containing preserving agents such as the esters of parahydroxybenzoic acid, benzalkonium chloride, benzyl alcohol, etc.

Following new regulations by the FDA (Food and Drug Administration) suspensions and aqueous solutions for inhalation must be sterile and without preserving agents.

The methods generally used to sterilize substances for inhalation such as corticosteroids have been the subject of a large number of studies. Although U.S. Pat. No. 6,464,958 describes the possibility of sterilizing powders by sonication, powders are generally sterilized by the action of ethylene oxide or gamma rays. The use of filtration for sterilizing of suspensions is disclosed in WO99132156 with a process requiring three steps. The first step consists of heating sterilization of a viscous enhancer solution; the second phase consists of filtering sterilization of an aqueous solution of the water-soluble active substance or substances. The third step consists of heating sterilizing an aqueous mixture of an active water-insoluble substance and of an electrolyte a hydrophilic surfactant is subsequently added to in aseptic conditions. The three mixtures are combined, in a sterile environment, to obtain a sterile suspension. WO00/74651 describes sterilizing method by filtration of an oily nasal solution containing water-insoluble drugs (for example beclomethasone dipropionate, budesonide, diazepam, etc.). WO01/07014 describes nasal solutions, sterilized by filtration, containing a steroid in a mixture of water and propylene glycol with pH=3.5-5.0.

Formulations for ocular use are described in WO02/40029 with a method encompassing a corticosteroid in salified form with excipients and/or diluents is added to an aqueous solution containing a polysaccharide. The solution obtained is sterilized by filtration. According to other methods, the sterilization process is carried out by precipitation with organic solvents as disclosed in U.S. Pat. No. 4,391,803 or by filtration of aqueous solutions as reported in JP 34000794.

WO90/06775 and U.S. Pat. No. 5,246,707 describe a method involving a sterilization of pharmaceutical formulation n the form of lyposomes.

U.S. Pat. No. 6,149,864 discloses a sterilization method involving the use of supercritical fluids. The method promotes diffusion of the supercritical fluid (for example, carbon dioxide) in the cells of the microorganisms, altering their relative pH and therefore killing them.

A description of the various techniques used is also provided in a review (J. of Drug Research (1969), 2(1-2), 103-8, pag. 93).

In the field of inhalation, the particles with therapeutic action and adjuvants insoluble in water generally must have a dimension between 1 and 5 μm.

Currently, interest has shifted towards particles with a dimension of between 3 and 5 μm to reduce deposit in the pulmonary alveoli during administration.

Generally particles reduction is realised by grinding and micronization and allow to obtain particles ranging from below 1 μm and 10 μm.

The use of sonication to reduce the dimensions of the particles is described in several patents and publications.

U.S. Pat. No. 5,091,187 describes a method for preparing injectable suspensions of microcrystals coated with phospholipids or other membrane-forming amphipathic lipids with the purpose of reducing tissue irritation. The size reduction of the crystalline drug particles from 50 μm to 10 μm is obtained by sonication in the presence of phospholipids or other amphipathic and non-amphipathic lipids.

The preparation of suspensions to be nebulized containing a corticosteroid suspended in water in the presence of surfactants, and whose size is reduced by sonication, is described in WO 99/18971.

WO00/38811 describes a procedure to reduce the dimension of active substances particles and carriers by sonication, for inhalation therapy. Various active substances are indicated, including Beclomethasone, Salbutamol, Fluticasone propionate, etc.

WO02/00199 describes a preparation method, which involves sonication to obtain the reduction of the crystalline size of active ingredients or carriers used for inhalation.

According to this method, the active ingredient (fluticasone propionate) is dissolved in hot acetone and subsequently cooled down to room temperature. A flow cell is filled with a 4:1 mixture of water and acetone (non-solvent and solvent) and a sonicator activated with power of 70-75 Watts. The solution of the active substance at room temperature is pumped into this solution by a first pump at a rate of 20 ml/minute and then cold water at a rate of 80 ml/minutes, is pumped into this solution by a second pump.

A crystalline suspension is rapidly formed, which the acetone is removed from by vacuum evaporation. Water is eliminated by freeze-drying and a fine white powder is obtained.

U.S. 2003044433 and US2003031719 describe, with a few variations, a preparation method of pharmaceutical suspensions wherein the active substance is more soluble in a mixture of organic solvent than in water.

The method has three steps: in the first step, the active substance is dissolved in the water soluble organic solvent, in the second step the first solution is mixed with water to obtain precipitation of the active substance and in the third step the solution is treated by sonication.

US2003003155 describes a method for reducing particles size below one μm. This consists in dissolving an organic compound the solubility of which is higher in a first water soluble solvent in comparison with a second aqueous solvent. The process consists in dissolving the active substance in the first water soluble solvent to obtain a solution and mixing the obtained solution with the second solvent to obtain a pre-suspension and, finally, reducing particle size to a value below 2 μm by means of mechanical energy.

In EP346953 sonication is employed to reduce the particles size of active substances while DE 3341001 relates to the preparation of an emulsion obtained by sonication.

In U.S. Pat. Nos. 5,803,966, 5,833,891 and 5,874,029 methods have been disclosed to reduce particle size by using supercritical fluids.

In any case, as it is shown by the processes briefly summarized above, sterilization and reduction of the particles take place with markedly distinct methods which have no elements in common.

Moreover, with the sonication technique, as it is also the case with micronization and grinding, it is not always possible to obtain products with a particle size distribution between 3 and 5 μm.

TECHNICAL PROBLEM

Therefore, there is a need to provide a single process for sterilization and reduction of the particle size of an active ingredient which also guarantees attainment of suspensions for inhalation, the particles size of said active ingredient being comprised between 3 and 5 μm.

SUMMARY OF THE INVENTION

The Applicant has now found a single sterilization and particle size reduction process wherein at least 80% of the particles have a diameter of between 3 and 5 μm.

The peculiarity of the present invention relates to the implementation of a method to obtain sterile particles of suitable dimensions for inhalation in aqueous suspension, with a single process which comprises dissolving a liposoluble active substance in an organic solvent, such as ethanol, adding one or more surfactants to facilitate the wettability of the active substance particles and, precipitation filtration by adding sterile deionized water under sonication. In this case the active substance, being insoluble in an aqueous environment, precipitates and forms a suspension, and the particles take the required size according to the ultrasonic power employed. The last part of the operation is conducted in a sterile environment.

DESCRIPTION OF THE INVENTION

In particular, the process of the present invention comprises the following steps:
a) dissolving the active ingredient in the minimum quantity of an alcoholic solvent, optionally in the presence of a polyol and adding at least one surfactant,
b) filtering the solution obtained in the previous step through a sterilizing filter,
c) adding the solution from step (b) to sterile water under sonication to directly obtain a suspension wherein the particles have a reduced diameter.

In step (a) the alcoholic solvent is preferably ethanol while the optional polyol, is preferably propylene glycol.

According to a particularly preferred embodiment of the present invention, a mixture of ethanol and propylene glycol is used.

Sorbitan trioleate, oleic alcohol, lecithin oleic acid, Tween etc., can for example be employed as the surfactant. Particularly preferred is ethoxylated castor oil available for sale with the trade name Cremophor EL.

The active substance insoluble in water is generally selected from the group consisting of steroid anti-inflammatory drug, anti-asthma drug etc.

Preferably, the active ingredient is dissolved in alcohol in weight ratios, with respect to the alcohol, ranging from 0.1 to 1. According to a particularly preferred embodiment, it is dissolved in ethanol in a weight ratio of 1:1.

In step (a), polyol is added in a weight ratio, with respect to the alcohol, ranging from 0.4 to 4.

According to a particularly preferred embodiment a propylene glycol/ethanol weight ratio of 3.75 is used.

The sterilizing filter employed in step (b) is a conventional filter which preferably retains particles with size higher than 0.22 μm.

Sterile water employed in step (c) is preferably sonicated for approximately 15 minutes.

The operating conditions for carrying out sonication are not critical for the purposes of the process of the present invention.

In any case, sonication in step (c) of the process of the present invention is preferably conducted at a frequency ranging from 20 to 40 kHz, a vibration wave length of between 35 and 70 μm and a power of between 500 and 3000 Watts. Optimal results are obtained employing the aforesaid operating parameters: frequency 20 kHz, power 600 Watts and, finally, wave length of 40 μm.

Preferably, particles size depends on operating conditions of sonication, which preferably fall within the aforesaid parameters. Moreover, another operating parameter capable of acting on the dimension of the particles of the active ingredient is the duration of sonication.

The duration of sonication, corresponding to a single sonication cycle (considered sonication time+pause time) is preferably comprised between 3 and 6 minutes. This sonication cycle (sonication+pause) can be repeated n times (with n ranging from 1 to 50) wherein n is a parameter depending on specific active ingredient, batch size, and the particle size distribution to be realised. Furthermore the sonication cycle may be carried out by means of either a sole or more horns.

Preferably the temperature of step (c) is controlled by means of suitable cooling system known in the state of the art. The process of the present invention makes it possible to obtain suspensions for inhalation containing the active ingredient in concentrations between 0.01 and 0.1% by weight, alcohol in concentrations between 0.01 and 0.4%, surfactants in concentrations between 0.04 and 0.4% by weight and optionally polyol, in concentrations between 0.04 and 0.4% by weight and the remaining to 100 parts by weight consists of sterile water.

The process according to the present invention makes also it possible to obtain suspensions for inhalation containing the active ingredient in concentrations between 0.01 and 0.1% by weight, alcohol in concentrations between 0.01 and 0.1%, surfactants in concentrations between 0.04 and 0.4% by weight and optionally polyol, in concentrations between 0.04 and 0.4% by weight and the remaining to 100 parts by weight consists of sterile water.

According to a particularly preferred embodiment, the process of the present invention makes it possible to obtain suspensions for inhalation for pharmaceutical use having the following concentration: active ingredient 0.04%, ethoxylated castor oil: 0.15%, ethanol: 0.04%, propylene glycol: 0.15%, sterile water q.s. to 100 parts by weight.

According to another particularly preferred embodiment the process of the present invention makes it possible to obtain suspensions for inhalation for pharmaceutical use having the following concentration: active ingredient 0.04%, ethoxylated castor oil: 0.15%, ethanol: 0.40%, propylene glycol: 0.15%, sterile water q.s. to 100 parts by weight.

The following examples are provided purely to facilitate the understanding of the invention, without being limiting for the subject thereof.

EXAMPLE 1

| | |
|---|---|
| Beclomethasone dipropionate (BDP) | 0.04% |
| Ethoxylated castor oil (*) | 0.15% |
| Propylene glycol | 0.15% |
| Ethanol | 0.04% |
| Sterile water q.s. to | 100 ml |

(*) Cremophor EL

Preparation Method

1) BDP is dissolved in Ethanol, propylene glycol and Cremophor EL are added and the resulting solution is mixed; it is then filtered through a sterilizing filter and the solution is collected into a suitable container in a sterile area.
2) The deionized sterile water is introduced in a suitable container and treated by sonication for approximately 15 minutes.
3) The mixture obtained as described in point 1) is added to the sterile and sonicated water under sonication.

The duration of sonication is between 3 and 6 minutes.

Operating Parameters

Wave length: 40 µm (instrument range: 35-70 µm)

Power of the horn: 600 Watts (instrument range: 500-3000 Watts)

Frequency of the horn: 20 kHz.

EXAMPLE 2

Operations are conducted in a similar way to those described in Example 1. The final formulation of the solution, expressed in %, is as follows:

| % by Weight | |
|---|---|
| Budesonide | 0.04% |
| Ethoxylated castor oil (*) | 0.15% |
| Propylene glycol | 0.15% |
| Ethanol | 0.04% |
| Sterile water q.s. to | 100 ml |

(*) Cremophor EL

EXAMPLE 3

Operations are conducted in a similar way to those described in Example 1. The final formulation of the solution, expressed in %, is as follows:

| % by weight | |
|---|---|
| Salbutamol | 0.04% |
| Ethoxylated castor oil (*) | 0.15% |
| Propylene glycol | 0.15% |
| Ethanol | 0.04% |
| Sterile water q.s. to | 100 ml |

(*) Cremophor EL

EXAMPLE 4

Beclomethasone dipropionate (BDP) 0.04%

| | |
|---|---|
| Ethoxylated castor oil (*) | 0.15% |
| Propylene glycol | 0.15% |
| Ethanol | 0.40% |
| Sterile water q.s. to | 100 ml |

(*) Cremophor EL

Preparation Method

BDP (2.8 g) is dissolved in ethanol (28 g), propylene glycol (10.5 g) and Cremophor EL (10.5 g) are added, and the mixture obtained is stirred and filtered through a sterilising filter (0.22 µm) and the solution obtained is collected in a suitable sterile container.

Deionised water is charged into a suitable sterile container and sonicated for about 15 minutes.

The mixture coming from step 1) is poured into sterile water coming from step 2), under sonication Operating Parameters Constant outlet power of horn 1200 W Horn frequency 20 KHz Sonicator is programmed as follows: sonication cycle 3 minutes (sonication time 1.5 minutes/pause time 1.5 minutes) n (=number of sonication cycles conducted): n=4 (sample A)

EXAMPLE 5

The operating conditions of Example 4 are repeated with the sole difference that n=8 (Sample B).

EXAMPLE 6

The operating conditions of Example 4 are repeated by carrying out a sonication cycles number n=15 (Sample C).

EXAMPLE 7

The operating conditions of Example 4 are repeated by carrying out a sonication cycles number n=22 (Sample D)

The experimental conditions of Example 4 are followed except for step 3).

In fact the mixture obtained in step 1) is introduced into sterile water and the active ingredient is left to crystallise for about 1 hour without sonicating. Subsequently, the suspension is sonicated using the same operating conditions of Example 4 and carrying out a number of sonication cycles n=22 (Sample E)

Results

The size analyses of the particles of samples A, B, C, D and E is conducted by using the Beckman Coulter LS Particles Size Analyzer.

The results are reported in the following table as D10, D50 and D90.

TABLE 1

| | Particle size (µm) | | |
|---|---|---|---|
| SAMPLE | D10 | D50 | D90 |
| A (n = 4) | 1.106 | 3.927 | 5.186 |
| B (n = 8) | 0.866 | 1.703 | 3.394 |
| C (n = 15) | 0.677 | 1.392 | 3.369 |
| D (n = 22) | 0.683 | 1.316 | 2.819 |
| E (n = 22) | 2.232 | 8.684 | 17.852 |

The comparative analysis evidences that, by using the operating conditions of the process according to the present invention (see Samples A, B, C and D) the particle size distribution of the particles may be modulated by varying the number of sonication cycles and therefore the sonication time.

In particular, as relevant the active ingredient type and batch size considered, the best results are achieved with the process conditions applied for Example 4) (Sample A).

The results reported with Sample E, compared with those of the preceding Samples, demonstrate that the sonication process, in order to be effective, must be carried out simultaneously to the precipitation of the active ingredients.

What is claimed is:

1. A sterile pharmaceutical inhalable aqueous suspension for treating asthma, consisting essentially of particles of an active ingredient insoluble in water selected from the group consisting of beclomethasone dipropionate (BDP), budesonide and salbutamol in a concentration between 0.01 and 0.1% by weight, an alcohol in a concentration between 0.01 and 0.1%, polyol in a concentration between 0.04 and 0.4%, a surfactant selected from the group consisting of ethoxylated castor oil, sorbitan trioleate, oleic alcohol, lecithin oleic acid, and polysorbates in a concentration between 0.04 and 0.4%, the remaining to 100 parts by weight consisting of sterile water, wherein at least 80% of the particles of said active ingredient insoluble in water have a diameter between 3 and 5 µm.

2. The sterile suspension of claim 1, wherein said alcohol is ethanol.

3. The sterile suspension of claim 1, wherein said polyol is propylene glycol.

4. The sterile suspension of claim 1, wherein said surfactant is ethoxylated castor oil.

5. The sterile suspension of claim 1, consisting essentially of 0.04% of the active ingredient, 0.15% of ethoxylated castor oil, 0.04% of ethanol, 0.15% of propylene glycol, and sterile water q.s. to 100 parts by weight.

* * * * *